US010159763B2

(12) United States Patent
Ou et al.

(10) Patent No.: US 10,159,763 B2
(45) Date of Patent: Dec. 25, 2018

(54) METHOD FOR PRODUCING ALPHA-CALCIUM SULFATE HEMIHYDRATE BONE GRAFT

(71) Applicant: 3D Global Biotech Inc., New Taipei (TW)

(72) Inventors: Keng-Liang Ou, New Taipei (TW); Chih-Hua Yu, New Taipei (TW); Yu-Hao Chan, New Taipei (TW); Wei-Jen Cheng, New Taipei (TW)

(73) Assignee: 3D GLOBAL BIOTECH INC., New Taipei (TW)

( * ) Notice: Subject to any disclaimer, the term of this patent is extended or adjusted under 35 U.S.C. 154(b) by 0 days.

(21) Appl. No.: 15/644,673

(22) Filed: Jul. 7, 2017

(65) Prior Publication Data

US 2018/0015200 A1     Jan. 18, 2018

(30) Foreign Application Priority Data

Jul. 12, 2016 (TW) .............................. 105121944 A (51) Int. Cl.
*A61L 27/04* (2006.01)
*A61L 27/58* (2006.01)
*C01F 11/46* (2006.01)

(52) U.S. Cl.
CPC ............ *A61L 27/047* (2013.01); *A61L 27/58* (2013.01); *C01F 11/466* (2013.01); *A61L 2430/02* (2013.01); *C01P 2002/72* (2013.01); *C01P 2002/88* (2013.01); *C01P 2004/03* (2013.01)

(58) Field of Classification Search
CPC .... A61L 27/047; A61L 27/58; A61L 2430/02; C01P 2004/03; C01P 2002/72; C01P 2002/88; C01F 11/466
See application file for complete search history.

(56) References Cited

U.S. PATENT DOCUMENTS

| 5,248,487 A    | * | 9/1993 | Bold  | ...................... C01F 11/466 106/786 |
| 2011/0189296 A1 | * | 8/2011 | Rauis | ....................... A61K 9/00 424/489 |

FOREIGN PATENT DOCUMENTS

DE     38 44 938 C2 *  9/1996  .......... A01K 1/0154

* cited by examiner

*Primary Examiner* — Timothy C Vanoy (57) ABSTRACT

The present invention discloses a method for producing the alpha-calcium sulfate hemihydrate bone graft, which comprises the following steps: mixing calcium sulfate dihydrate and deionized water to produce calcium sulfate dihydrate paste; stirring and heating the calcium sulfate dihydrate paste at least 160° C. within 100-350 psi to produce the conversion calcium sulfate hemihydrate, filtering the conversion calcium sulfate hemihydrate with high temperature to produce the filtered calcium sulfate hemihydrate, and washing the filtered calcium sulfate hemihydrate by absolute alcohol to get the alpha-calcium sulfate hemihydrate bone graft. The present invention does not use any catalyst, possesses a high purity, high mechanical strength, and good biocompatibility, facilitates bone growth and angiogenesis, requires only 31° C., the highest temperature, during the curing process. It makes the present invention more secure in the biomedical applications.

10 Claims, 11 Drawing Sheets

| Test project | USP 38 Calcium Sulfate Specification | Test result | Detection limit | Unit |
|---|---|---|---|---|
| arsenic (As) | < 10.0 | N.D. | 2.00 | ppm(mg/kg) |
| lead(Pb) | < 10.0 | N.D. | 2.00 | ppm(mg/kg) |
| mercury(Hg) | < 10.0 | N.D. | 2.00 | ppm(mg/kg) |
| cadimum(Cd) | < 10.0 | N.D. | 2.00 | ppm(mg/kg) |
| iron(Fe) | < 100.0 | 15.5 | 2.00 | ppm(mg/kg) |

| Comparison | Original femur length | After femur length | Length increase |
|---|---|---|---|
| Without using any bone powder(a) | 18 mm | 18 mm | + 0 mm |
| Commercially available bone powder (b) | 23 mm | 24 mm | + 1 mm |
| Bone powder of the present invention (c) | 19 mm | 21 mm | + 2 mm |

METHOD FOR PRODUCING ALPHA-CALCIUM SULFATE HEMIHYDRATE BONE GRAFT

BACKGROUND OF THE INVENTION

1. Field of the Invention

The present invention relates to a method for producing a calcium sulfate hemihydrate bone graft, more particularly, to a method for producing a biomedical-used α-calcium sulfate hemihydrate bone graft.

2. Description of the Prior Art

Bones are one of the crucial components of the human body. With the progress of modern medicine, bone repair and reconstruction have become an important research direction for orthopedics. Common bone grafts can be divided into autogenic, allogenic and heterogenic. Autologous bone is extracted from the patient's own body, with the best biocompatibility, but requires secondary surgery to obtain. Besides, the surgery takes a few days for wound healing, and may lead to other serious complications. Allografts are bone tissue donated by other people, with considerable biocompatibility, but often with insufficient supply. Heterogenous bones are derived from a variety of species, with sufficient supply, but also come with large immunological rejection. Besides, allografts and heterogenous bone are likely to cause the occurrence of infectious diseases and allergies.

Although the above three kinds of bone grafts are with stable results, due to the requirement of secondary surgery of autologous bone and insufficient supply as well as possible new infectious diseases of allograft and heterogenous bones, it causes patients nervous when choosing the bone grafts. As a result, biochemical synthetic matrix has become a new alternative.

There are two categories of biochemical synthetic matrix, including non-resorbable and resorbable matrix. The non-resorbable representative is Hydroxyapatite (HA). HA implantation in bone defect area can form a stable support in period of bone repair, but the bone ridge will be increased after the bone repair due to the non resorbability of HA, and HA doesn't have any osteoinductivity.

Calcium sulfate salts are common resorbable bone substitutes. This type of bone substitute is the better bone graft as it can gradually be absorbed by the body after implantation in the bone defect, and has the effect of inducing bone growth.

However, due to ordinary calcium with uneven crystal structure and difference on degradation rate, the absorption is too slow and then hinders the new bone formation. In the conventional technique, the biomedical-used α-calcium sulfate hemihydrate is often prepared by using a catalyst or other non-calcium sulfate salts. When those used on human body, it may cause bone substitutes be contaminated by impurities and lead to negative reactions on human body.

Thus, the above-mentioned technology still has many disadvantages, and it is not a good design. Therefore, it needs to be improved. In conclusion, the present invention provides a method for directly producing the α-calcium sulfate hemihydrate bone graft by using only calcium sulfate salt raw material.

SUMMARY OF THE INVENTION

Therefore, the present inventor with many years engaged in the manufacture and development of related products and design experience went through the detailed design and careful assessment to finally confirm that the present invention is practically usable.

A primary object of the present invention is to provide a method for producing the α-calcium sulfate hemihydrate bone graft. In an embodiment of the present invention, the method comprises the following steps: $S_1$: mixing calcium sulfate dihydrate and pure water to produce a calcium sulfate dihydrate paste; $S_2$: stirring and heating the calcium sulfate dihydrate paste to at least 160° C. for producing a conversion calcium sulfate hemihydrate; $S_3$: filtering the conversion calcium sulfate hemihydrate with a high temperature to produce a filtered calcium sulfate hemihydrate; and $S_4$: washing the filtered calcium sulfate hemihydrate by an absolute alcohol to generate the α-calcium sulfate sulfate hemihydrate bone graft. In step $S_2$, the calcium sulfate dihydrate paste is stirred by a magnetic stir bar. Besides, the step $S_2$ is for heating the calcium sulfate dihydrate paste to 160° C. and then maintaining at the temperature for 10 minutes to produce the conversion calcium sulfate hemihydrates. Therefore, the conversion calcium sulfate hemihydrates are comprised with the α-calcium sulfate hemihydrate bone graft and other by-products that we need. Besides, the step $S_2$ is executed in a Teflon tube and the tube pressure in the Teflon tube is set between 100 psi and 350 psi.

The present invention relates to a method for producing the α-calcium sulfate hemihydrate bone graft and further comprises the following step of $S_5$: drying the α-calcium sulfate hemihydrate bone graft, wherein the step $S_5$ is for drying the alpha-calcium sulfate hemihydrate bone graft at 60° C. to 80° C. for 6 hours to 8 hours.

According to the measurement results of the SGS Taiwan Ltd., the purity of the present invention α-calcium sulfate hemihydrate bone graft converted from calcium sulfate dihydrate yields above 97 weight percent (97 wt %). Impure ingredients including arsenic, lead, mercury, cadmium are less than 2 ppm, in line with the USP 38 Calcium Sulfate Specification (USP 38 Calcium Sulfate specifications of arsenic, lead, mercury, cadmium are required to be less than 10 ppm). The iron content is about 15.5 ppm, which is also in line with the USP 38 Calcium Sulfate Specification (iron is required to be less than 100 ppm in accordance with the USP 38 Calcium Sulfate specification).

Besides, in physical properties detections, the present invention α-calcium sulfate hemihydrate bone graft has a curing time of about 6.5 to 7.5 minutes. In the curing time of 25 minutes, its temperature is risen about 8° C. and the maximum temperature is about 31° C. The compressive strength of the above mentioned bone craft is 6.62±1.01 MPa by controlling the concentration of curing powder with 0.6 mL/g.

In animal experiments, by using the above mentioned bone craft in the bone defect of chicken femur, the results show obvious reactions on periosteal regeneration, angiogenesis and osteogenesis, wherein the femur length grows from 19 mm to 21 mm. The increase of 2 mm is more effective than that commercially available bone powder of 1 mm (from original 23 mm to 24 mm).

By the nature of the above, the present invention α-calcium sulfate hemihydrate bone graft can be applied to the implementation on biomedical bone powder, including dental implant surgery, bone transplantation and osteosynthesis surgery. Furthermore, the implementation mentioned above can effectively shorten the operation time for doctors, wherein the temperature of the use is lower than the average body temperature of 37° C., so that the patient will not suffer physical damage caused by severe changes in temperature.

Compared with the conventional technique, the method for producing α-calcium sulfate hemihydrate bone graft derives from the calcium sulfate dihydrate paste, including promoting the reaction evenly by stirring in high pressure, filtering the conversion calcium sulfate hemihydrate a high temperature, and washing the filtered calcium sulfate hemihydrate by an absolute alcohol. The present invention uses pure water and biomedical-used absolute alcohol rather than catalyst and other heterogeneous substances, hence the impurities in the preparation process can be effectively reduced. Therefore, the method for producing biomedical-used α-calcium sulfate hemihydrate bone graft can be more secure.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1:
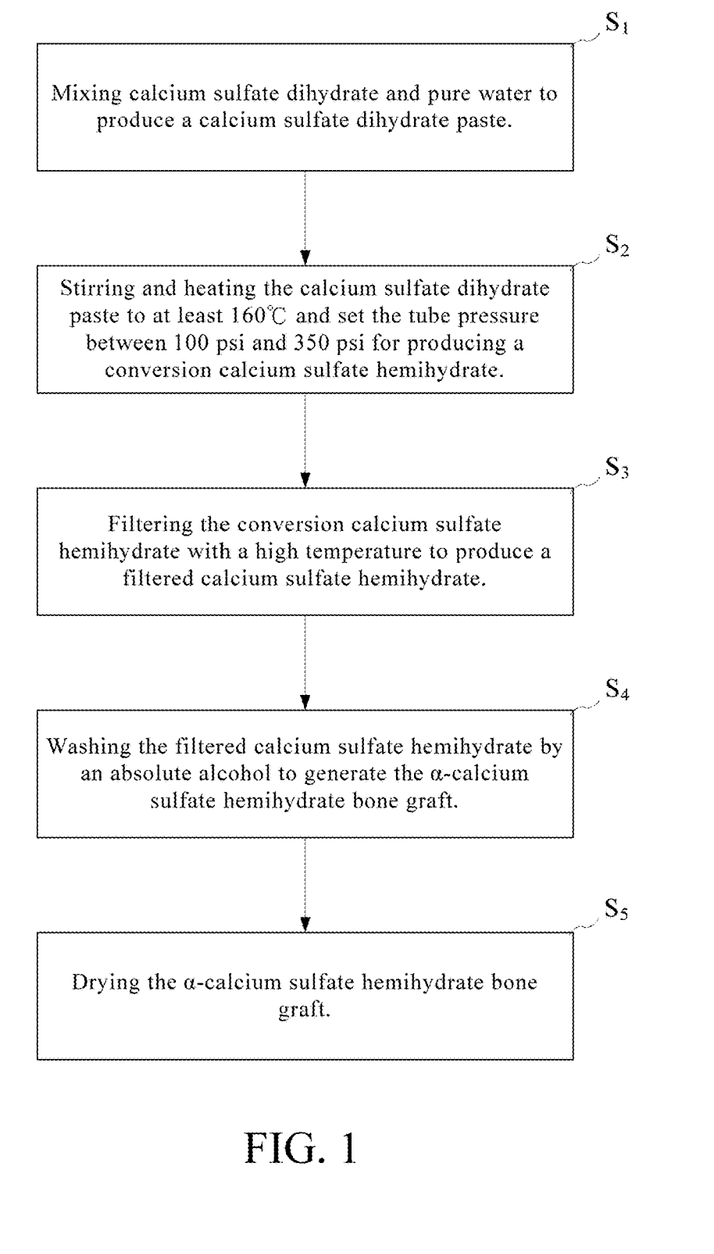
FIG. 1 shows a flow diagram of the method for producing an α-calcium sulfate hemihydrate bone graft in an embodiment of the present invention.

Please refer to FIG. 1. FIG. 1 shows a flow diagram of the method for producing an α-calcium sulfate hemihydrate bone graft in an embodiment of the present invention. In an embodiment of the present invention, the method comprises the following steps: $S_1$: mixing calcium sulfate dihydrate and pure water to produce a calcium sulfate dihydrate paste, wherein the pure water mentioned above can either be sterile water or deionized water; $S_2$: stirring and heating the calcium sulfate dihydrate paste to at least 160° C. for producing a conversion calcium sulfate hemihydrate; $S_3$: filtering the conversion calcium sulfate hemihydrate with a high temperature to produce a filtered calcium sulfate hemihydrate; and $S_4$: washing the filtered calcium sulfate hemihydrate by an absolute alcohol to generate the α-calcium sulfate hemihydrate bone graft. In step $S_2$, the calcium sulfate dihydrate paste is stirred by a magnetic stir bar. Besides, the step $S_2$ is for heating the calcium sulfate dihydrate paste to 160° C. and then maintaining at the temperature for 10 minutes to produce the conversion calcium sulfate hemihydrates. Therefore, the conversion calcium sulfate hemihydrates are comprised with the α-calcium sulfate hemihydrate bone graft and other by-products that we need.

Furthermore, the step $S_2$ is for heating the calcium sulfate dihydrate paste to 160° C. in 20 minutes and then maintaining at the temperature for 10 minutes to produce the conversion calcium sulfate hemihydrates. Besides, the step $S_2$ is executed in a Teflon tube and the tube pressure in the Teflon tube is set between 100 psi and 350 psi. In an embodiment, the method may include heating 1.5 g of calcium sulfate dihydrate and 10 ml of deionized water in a Teflon tube with a magnetic stir bar inside. The output power of the microwave device may be set to 800 watts (W), the pressure in the Teflon tube is set between 100 psi and 350 psi. The calcium sulfate dihydrate paste may be heated to 160° C. by microwave in 20 minutes and then kept at the temperature for 10 minutes to produce the conversion calcium sulfate hemihydrates. The specifications of the magnetic stir bar mentioned above may be the diameter of 6 mm and the length of 15 mm, wherein the stirring process may be assisted by rotating the magnetic stir bar or adding other mechanical swing or other stirring methods.

In an embodiment, the high temperature to produce a filtered calcium sulfate hemihydrate at step $S_3$ is above 100° C. In an embodiment, the conversion calcium sulfate hemihydrate is subjected to a cooling filtration action at 100° C. or higher by means of an evacuating filtration method to obtain the filtered calcium sulfate hemihydrate.

In addition, the method for producing an alpha-calcium sulfate hemihydrate bone graft, further comprising the following step of: $S_5$: drying the alpha-calcium sulfate hemihydrate bone graft. The drying temperature of drying the alpha-calcium sulfate hemihydrate bone graft may be 60° C. to 80° C. for 6 hours to 8 hours.

In an embodiment, the α-calcium sulfate hemihydrate bone graft may be dried through an oven, wherein the drying temperature may be 60° C. to 80° C. for 6 hours to 8 hours. Then, through procedures with grinding, filtering, and packaging, the dried α-calcium sulfate hemihydrate bone graft can be applied to biomedical use.

Figure 2:
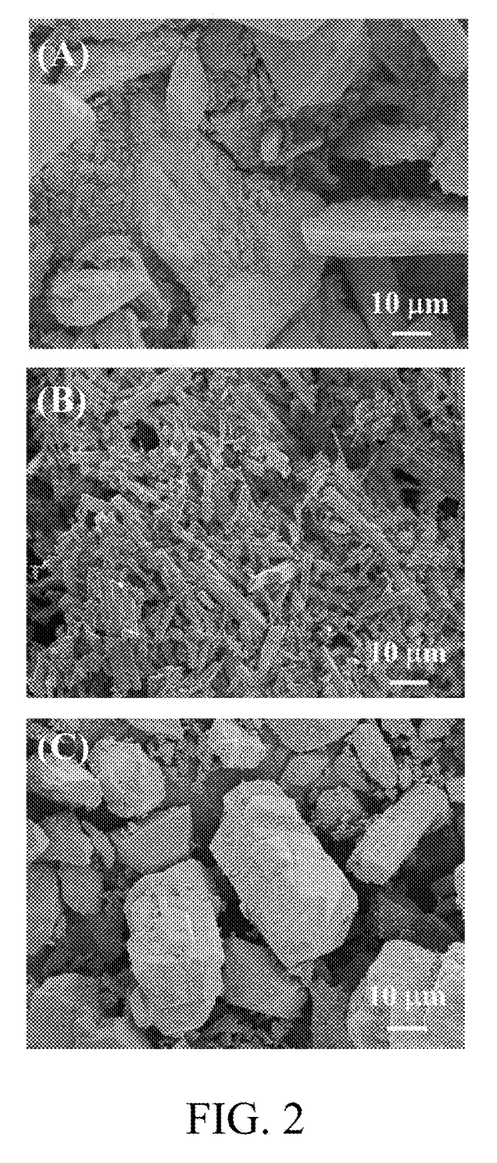
FIG. 2 shows a surface diagram of calcium sulfate dihydrate and different kinds of calcium sulfate hemihydrate.

Please refer to FIG. 2. FIG. 2 shows a surface diagram of calcium sulfate dihydrate and different kinds of calcium sulfate hemihydrate, wherein the diagram is taken on a scanning electron microscope (SEM) with a scale of 10 μm.

According to the scanning results of SEM, the calcium sulfate dihydrate raw material as shown in (A) in FIG. 2, is in the form of crystalline aggregates having the appearance of flaky cracks; (B) in FIG. 2 is the present invention α-calcium sulfate hemihydrate bone graft with the structure of columnar crystal, having an average size of 10 μm; (C) in FIG. 2 is the commercially available α-calcium sulfate hemihydrate bone graft with the structure of granular crystal, having an average size of 20 μm. Compared with the commercially available α-calcium sulfate hemihydrate bone graft, the structure of the present invention is more conducive to reduce the size of the micro-channel after curing, that is, to improve the structural strength of curing.

Figure 3:
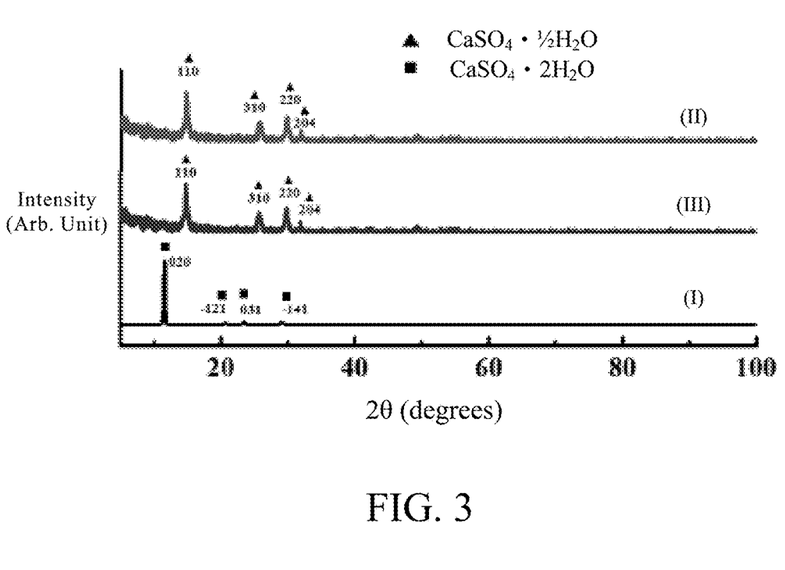
FIG. 3 shows an X-ray diffraction diagram (XRD) of calcium sulfate dihydrate and different calcium sulfate hemihydrate.

Please refer to FIG. 3. FIG. 3 shows an X-ray diffraction (XRD) diagram of calcium sulfate dihydrate and different kinds of calcium sulfate hemihydrate, wherein the abscissa is 2θ degrees, and the ordinate is the intensity (Arb. Unit). (I) in FIG. 3 is the XRD of calcium sulfate dihydrate raw material. (II) in FIG. 3 is the XRD of the present invention α-calcium sulfate hemihydrate bone graft. (III) in FIG. 3 is the XRD of the commercially available α-calcium sulfate hemihydrate bone graft. Compared with (I) and (III) in FIG. 3, the present invention (II) in FIG. 3 is similar to the commercially available α-calcium sulfate hemihydrate bone graft and has no characteristic peak (202) signal of calcium sulfate dihydrate raw material. It is presumed that the present invention has been completely converted into α-calcium sulfate hemihydrate bone graft.

Figure 4:
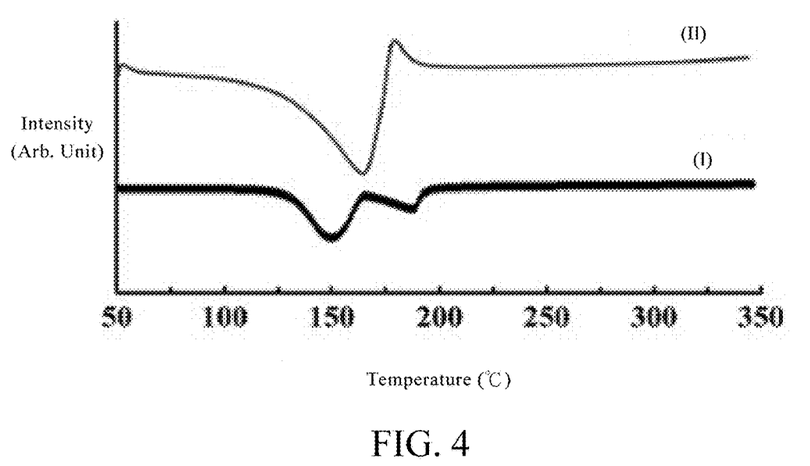
FIG. 4 shows a differential scanning calorimeter (DSC) schematic diagram of the calcium sulfate dihydrate and the present invention α-calcium sulfate hemihydrate bone graft.

Please refer to FIG. 4. FIG. 4 shows a differential scanning calorimeter (DSC) schematic diagram of the calcium sulfate dihydrate and the present invention α-calcium sulfate hemihydrate bone graft, wherein the abscissa is the temperature (° C.), and the ordinate is the intensity (Arb. Unit). (I) in FIG. 4 is the DSC signal of calcium sulfate dihydrate raw material. (II) in FIG. 4 is the DSC signal of the present invention α-calcium sulfate hemihydrate bone graft. According to FIG. 4, there is no obvious reaction peak at about 150° C. and about 195° C., whereby it is presumed that the product of the α-calcium sulfate hemihydrate ((II) in FIG. 4) has no residual calcium sulfate dihydrate raw material ((I) in FIG. 4).

Figure 5:
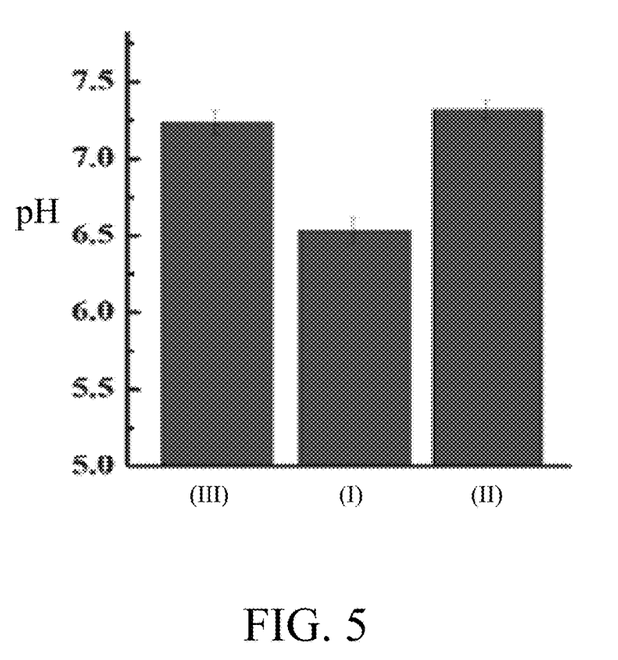
FIG. 5 shows a pH comparison diagram of calcium sulfate dihydrate and different kinds of calcium sulfate hemihydrate.

Please refer to FIG. 5. FIG. 5 shows a pH comparison diagram of calcium sulfate dihydrate and different kinds of calcium sulfate hemihydrate, wherein the abscissa shows different components, and the ordinate is the pH value. (I) in FIG. 5 is the pH value of the calcium sulfate dihydrate raw material. (II) in FIG. 5 is the pH value of the present invention α-calcium sulfate hemihydrate bone graft. (III) in FIG. 5 is the pH value of the commercially available α-calcium sulfate hemihydrate bone graft. Each bar is measured five times. The present invention α-calcium sulfate hemihydrate (II) in FIG. 5 and the commercially available α-calcium sulfate hemihydrate (III) in FIG. 5 have the same pH value as the neutral to weak base, while the calcium sulfate dihydrate raw material shows acid. It is presumed that the product of the α-calcium sulfate hemihydrate ((II) in FIG. 5) has no residual calcium sulfate dihydrate raw material ((I) in FIG. 5).

Figure 6:
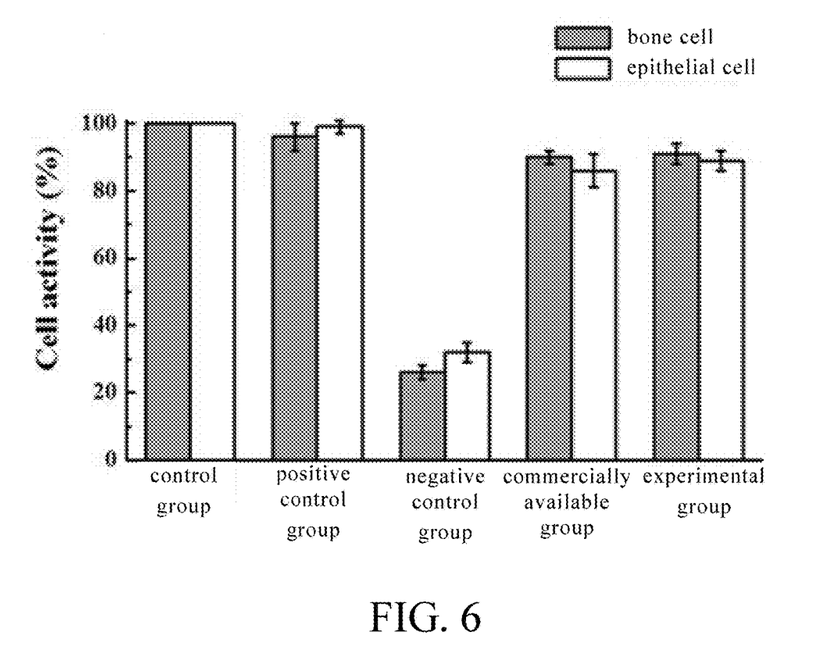
FIG. 6 shows a test result diagram on cytotoxicity of the present invention α-calcium sulfate hemihydrate bone graft.

Please refer to FIG. 6. FIG. 6 shows a test result diagram on cytotoxicity (according to ISO 10993-5 standard test) of the present invention α-calcium sulfate hemihydrate bone graft. FIG. 6 shows the test result of the bone cell and epithelial cells cultured in vitro in the α-calcium sulfate hemihydrate extract, wherein the ordinate shows cell activity, the abscissa shows different groups, including the control group, positive control group (HDPE, high density polyethylene), negative control group (ZDBC, zinc dibutyldithiocarbamate), commercially available group (commercially available α-calcium sulfate hemihydrate), and an experimental group (prepared by the present invention of α-calcium sulfate hemihydrate bone graft). According to the test result of FIG. 6, it is presumed that the product of the α-calcium sulfate hemihydrate (the experimental group shows cell viability above 70%) has no cytotoxicity.

Figure 7:
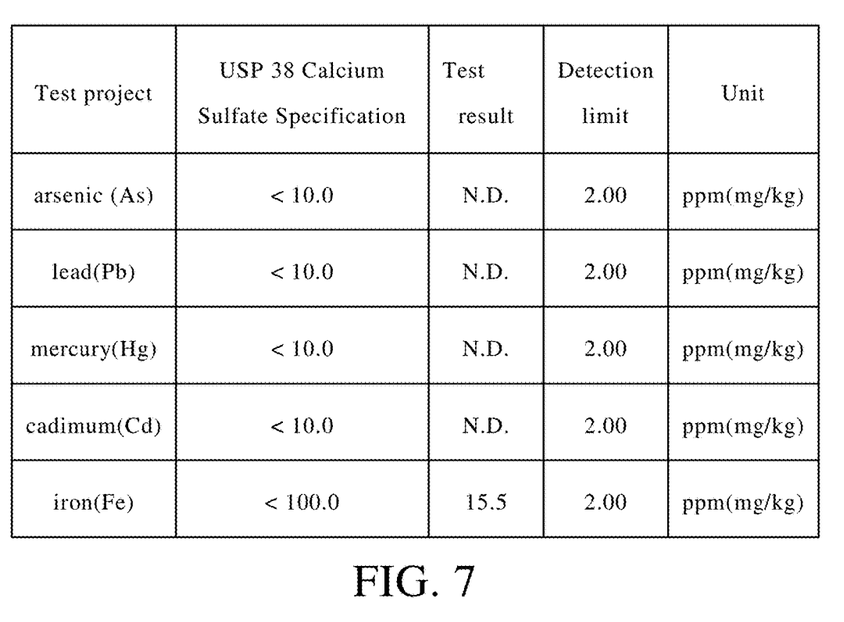
FIG. 7 shows a concentration comparison diagram on different impurities of the present invention α-calcium sulfate hemihydrate bone graft.

Please refer to FIG. 7. FIG. 7 shows a concentration comparison diagram on different impurities of the present invention α-calcium sulfate hemihydrate bone graft. According to the measurement results of the SGS Taiwan Ltd., the purity of the present invention α-calcium sulfate hemihydrate bone graft converted from calcium sulfate dihydrate yields above 97 weight percent (97 wt %). Impure ingredients including arsenic, lead, mercury, and cadmium are less than 2 ppm, in line with the USP 38 Calcium Sulfate Specification (USP 38 Calcium Sulfate specifications of arsenic, lead, mercury, and cadmium are required to be less than 10 ppm). The iron content is about 15.5 ppm, which is also in line with the USP 38 Calcium Sulfate Specification (iron is required to be less than 100 ppm in accordance with the USP 38 Calcium Sulfate specification). The minimum detection limit for each element is 2.0 ppm.

Besides, in physical properties detections, the present invention α-calcium sulfate hemihydrate bone graft has a curing time of about 6.5 to 7.5 minutes (in comparison with about 15 to 20 minutes of commercially available α-calcium sulfate hemihydrate). In the curing time of 25 minutes, its temperature rises by about 8° C. and a maximum temperature of about 31° C. The compressive strength of the present invention bone craft is 6.62±1.01 MPa by controlling the concentration of curing water powder with 0.6 mL/g.

Figure 8:
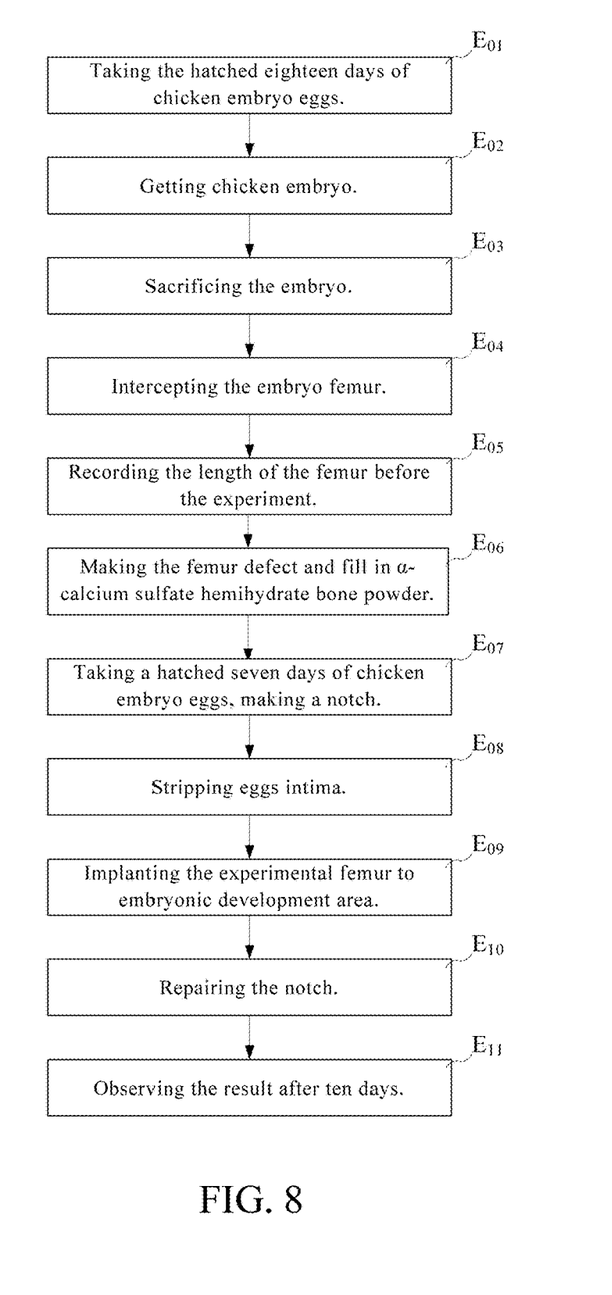
FIG. 8 shows a flow diagram of the animal experiments by using different kinds of α-calcium sulfate hemihydrate bone graft.

Please refer to FIG. 8. FIG. 8 shows a flow diagram of the animal experiments by using different kinds of α-calcium sulfate hemihydrate bone grafts, more particularly, by compared with using the present invention α-calcium sulfate hemihydrate bone graft. The animal experiment is conducted by using chorioallantoic membrane (CAM) of the chicken embryo, wherein the bone regeneration and angiogenesis are about to be confirmed. The animal experiment further comprises the following step of $E_{01}$: taking the hatched eighteen days of chicken embryo eggs; $E_{02}$: getting chicken embryo; $E_{03}$: sacrificing the embryo; $E_{04}$: intercepting the embryo femur; $E_{05}$: recording the length of the femur before the experiment; $E_{06}$: making the femur defect and fill in α-calcium sulfate hemihydrate bone powder; $E_{07}$: taking a hatched seven days of chicken embryo eggs, making a notch; $E_{08}$: stripping eggs intima; $E_{09}$: implanting the experimental femur to embryonic development area; $E_{10}$: repairing the notch; and $E_{11}$: observing the result after ten days.

Figure 9:
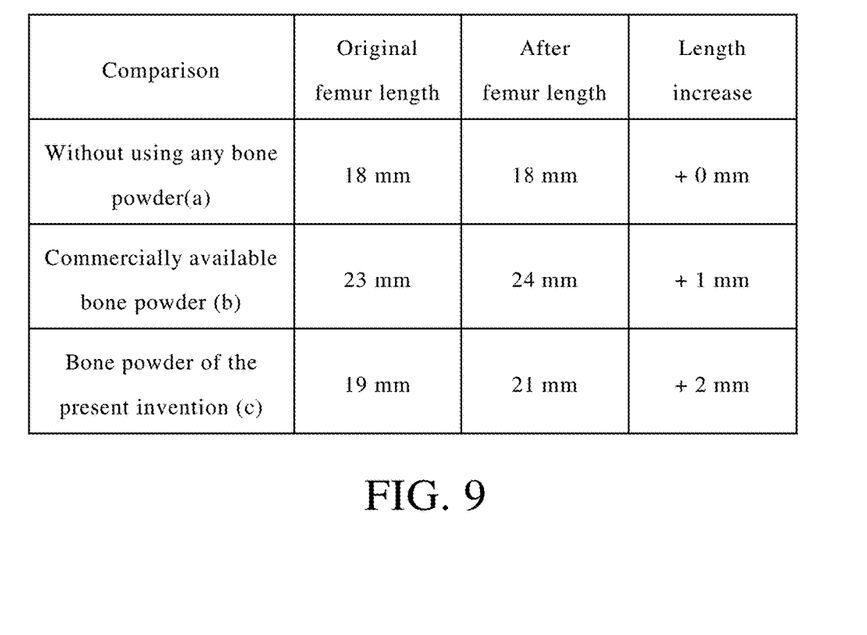
FIG. 9 shows a comparison diagram of the femur length after ten days of incubation in animal experiments using different kinds of α-calcium sulfate hemihydrate bone graft.
Figure 10:
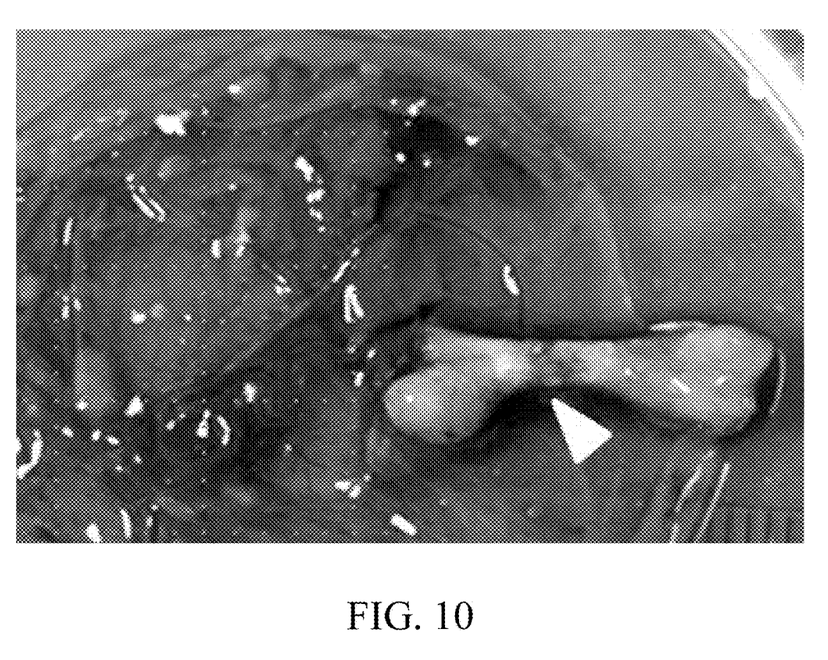
FIG. 10 shows a schematic diagram of bone growth and angiogenesis after ten days of incubation in animal experiments using the present invention α-calcium sulfate hemihydrate bone graft.
Figure 11:
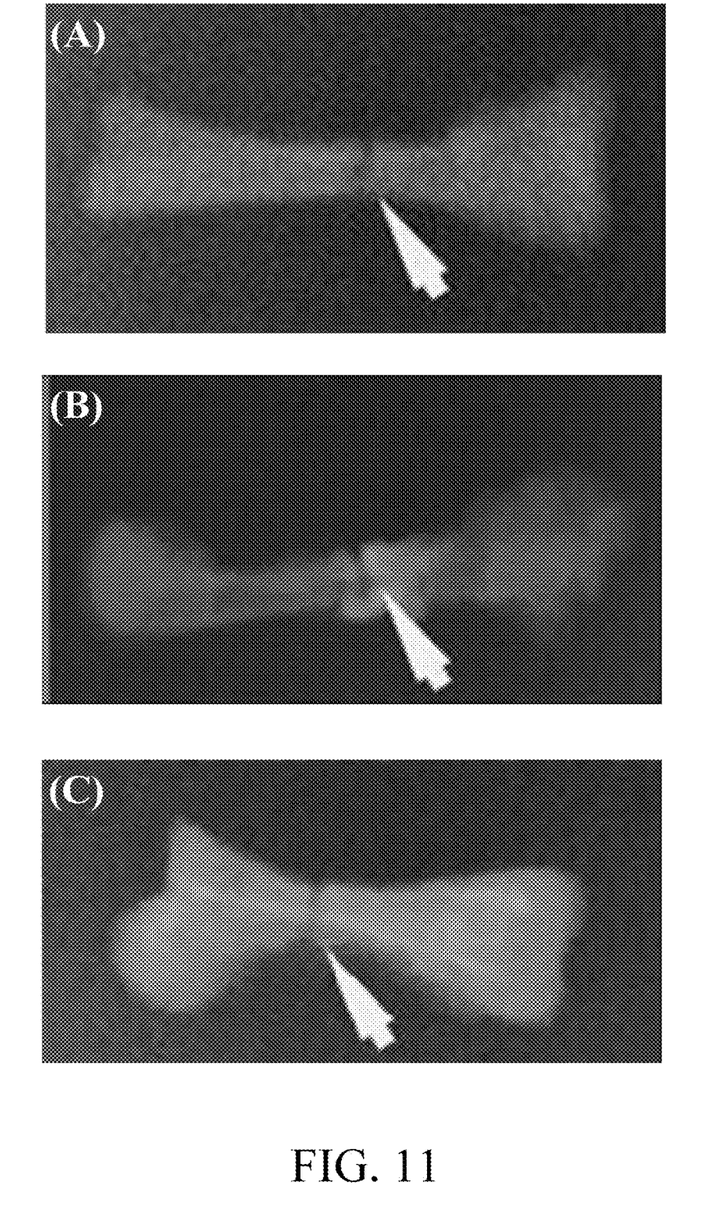
FIG. 11 shows an X-ray diagram of the femur after ten days of incubation in animal experiments using different kinds of α-calcium sulfate hemihydrate bone graft.

Please refer to FIG. 9, FIG. 10, and FIG. 11. FIG. 9 shows a comparison diagram of the femur length after ten days of incubation in animal experiments using different kinds of α-calcium sulfate hemihydrate bone grafts. FIG. 10 shows a schematic diagram of bone growth and angiogenesis after ten days of incubation in animal experiments using the present invention αcalcium sulfate hemihydrate bone graft. FIG. 11 shows an X-ray diagram of the femur after ten days of incubation in animal experiments using different kinds of α-calcium sulfate hemihydrate bone graft. In the observation results after ten days of incubation, the length of the femur shows no change of 18 mm to 18 mm without using α-calcium sulfate hemihydrate bone powder (chart (a)). Besides, the bone defect has obvious reactions on periosteal regeneration, angiogenesis and osteogenesis when using the present invention α-calcium sulfate hemihydrate bone graft as bone powder (chart (c)) on bone defect of the chicken femur (arrow mark), wherein the femur length grows from 19 mm to 21 mm. The increase of 2 mm is more effective than that commercially available bone powder (chart (b)) of 1 mm (from original 23 mm to 24 mm).

In conclusion, the present invention α-calcium sulfate hemihydrate bone graft can be applied to the implementation on biomedical bone powder, including dental implant surgery, bone transplantation and osteosynthesis surgery. Furthermore, the implementation mentioned above can effectively shorten the operation time for doctors, wherein the temperature of the use is lower than the average body temperature of 37° C., so that the patient will not suffer physical damage caused by severe changes in temperature.

Compared with the conventional technique, the method for producing α-calcium sulfate hemihydrate bone graft from the calcium sulfate dihydrate paste, including promoting the reaction evenly by stirring in high pressure, filtering the conversion calcium sulfate hemihydrate under high temperature, and washing the filtered calcium sulfate hemihydrate by an absolute alcohol. The present invention uses pure water and biomedical-used absolute alcohol rather than catalyst and other heterogeneous substances, hence the impurities in the preparation process can be effectively reduced. Therefore, the method for producing biomedical-used α-calcium sulfate hemihydrate bone graft can be more secure.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A method for producing an alpha-calcium sulfate hemihydrate bone graft, comprising the following steps of:

$S_1$: mixing calcium sulfate dihydrate and pure water to produce a calcium sulfate dihydrate paste;

$S_2$: stirring and heating the calcium sulfate dihydrate paste to at least 160° C. for producing a conversion calcium sulfate hemihydrate;

$S_3$: filtering the conversion calcium sulfate hemihydrate with a high temperature to produce a filtered calcium sulfate hemihydrate; and $S_4$: washing the filtered calcium sulfate hemihydrate by an absolute alcohol to generate the alpha-calcium sulfate hemihydrate bone graft.

2. The method of claim 1, wherein the step $S_2$ is for stirring the calcium sulfate dihydrate paste by a magnetic stir bar.

3. The method of claim 1, wherein the step $S_2$ is for heating the calcium sulfate dihydrate paste to 160° C. and then maintaining at the temperature for 10 minutes to produce the conversion calcium sulfate hemihydrate.

4. The method of claim 3, wherein the step $S_2$ is for heating the calcium sulfate dihydrate paste to 160° C. in 20 minutes and then maintaining at the temperature for 10 minutes to produce the conversion calcium sulfate hemihydrate.

5. The method of claim 1, wherein the pure water is sterile water or de-ionized water.

6. The method of claim 1, wherein the step $S_2$ is executed in a Teflon™ tube.

7. The method of claim 6, wherein a tube pressure in the Teflon™ tube is between 100 psi and 350 psi.

8. The method of claim 1, wherein, in the step of $S_3$, the high temperature for filtering the conversion calcium sulfate hemihydrate is over than 100° C.

9. The method of claim 1, further comprising the following step of:

$S_5$: drying the alpha-calcium sulfate hemihydrate bone graft.

10. The method of claim 9, wherein the step $S_5$ is for drying the alpha-calcium sulfate hemihydrate bone graft at 60° C. to 80° C. for 6 hours to 8 hours.

* * * * *